United States Patent [19]

Schraven et al.

[11] Patent Number: 5,942,415
[45] Date of Patent: Aug. 24, 1999

[54] SKAP55 COMPOSITIONS AND METHODS OF USE THEREFOR

[76] Inventors: Burkhart Schraven, Nadlerstrasse 5, 68526 Ladenburg, Germany; Anne Marie-Cardine, 19 Boulevard Jean Mermoz, 22700 Perros-Guirec, France; Stefan Meuer, Posseltstrasse 8, 69120 Heidelberg; Henning Kirchgessner, Langgasse 14, 69207 Sandhausen, both of Germany

[21] Appl. No.: 08/713,636

[22] Filed: Sep. 13, 1996

[51] Int. Cl.⁶ .......................... C12P 21/06; C07H 21/04; C12N 1/20
[52] U.S. Cl. ...................... 435/69.1; 435/325; 435/252.3; 435/252.33; 435/320.1; 536/23.1; 536/23.4; 536/23.5; 530/350
[58] Field of Search .......................... 424/9, 1; 435/69.1, 435/172.1, 325, 320.1, 194, 252.3, 252.33; 514/414; 536/23.5, 23.1, 23.4; 530/350

[56] References Cited

U.S. PATENT DOCUMENTS 5,434,064  7/1995  Schlessinger et al. ................ 435/172.3

OTHER PUBLICATIONS

Hillier et al (1995) EST database accession R01170, R01698, R01281.
Macke et al (1996) EST database accession W25899.
Ishino et al (1995) Oncogene 11:2331–2338 "Molecular cloning of a cDNA encoding a phosphoprotein, EFS, which contains . . . ".
Arni et al (1993) Oncogene 8:2485–2491 "Selective association of the p59$^{fyn}$ tyrosine kinase with murine T lymphoma membrane phosphoproteins".
Hillier et al., EST database Accession No. R02640 (1995).
Da Silva, A.J. et al. (1992) "Engagement of the TcR/CD3 Complex Stimulates p59$^{fyn(1)}$ Activity: Detection of Associated Proteins at 72 and 120–130 KD" *Molecular Immunology* 29, (12), 1417–1425.
Da Silva, A.J. et al. (1993) "T Cell Receptor ζ/CD3–p59$^{fyn(1)}$—Associated p120/130 Binds to SH2 Domain of p59$^{fyn(T)}$" *J. Exp. Med.* 178:2107–2113.
Ellis, C. et al. (1996) "A Juxtamembrane Autophosphorylation Site in the Eph Family Receptor Tyrosine Kinase, Sek, Mediates High Affinity Interaction With p59$^{fyn}$" *Oncogene* 12:1727–1736.
Frech, M. et al. (1995) "Pleckstrin Homology Domains" *Biochemical Society Transactions* 23:616–618.
Ingley, E. et al. (1994) "Pleckstrin Homology (PH) Domains in Signal Transduction" *Journal of Cellular Biochemistry* 56:436–443.
Koch, C.A. et al. (1991) "SH2 and SH3 Domains: Elements That Control Interactions of Cytoplasmic Signaling Proteins" *Science* 252:668–674.
Marie–Cardine, A. et al (1995) "Human T Lymphocyte Activation Induces Tyrosine Phosphorylation of α–Tubuline and Its Association With the SH2 Domain of the p59$^{fyn}$ Protein Tyrosine Kinase" *Eur. J. Immunol* 25:3290–3297.
Prasad, K.V.S. et al. (1993) "Src–homology 3 Domain of Protein Kinase p59$^{fyn}$ Mediates Binding To Phosphatidylinositol 3–Kinase in T Cells" *Proc. Natl. Acad. Sci. USA* 90:7366–7370.
Shaw, G. et al. (1996) "The Pleckstrin Homology Domain: An Intriguing Multifunctional Protein Module" *BioEssays* 18,(1):35–46.
Songyang, Z. et al. (1993) "SH2 Domains Recognize Specific Phosphopeptide Sequences" *Cell* 72:767–778.
Sun, X.J. et al. (1996) "The Fyn Tyrosine Kinase Binds Irs–1 and Forms A Distinct Signaling Complex During Insulin Stimulation" *The Journal of Biological Chemistry, 271,* (16):10583–10587.
Tsygankov, A.Y. et al. (1994) "Activation–Dependent Tyrosine Phosphorylation of Fyn–Associated Proteins In T Lymphocytes" 269, (10):7792–7800.

*Primary Examiner*—Robert A. Wax
*Assistant Examiner*—Nashaat T. Nashed
*Attorney, Agent, or Firm*—Lahive & Cockfield, LLP

[57] ABSTRACT

Isolated nucleic acid molecules encoding a novel protein, SKAP55, that interacts with the protein tyrosine kinase Fyn, are disclosed. SKAP55 protein has an apparent native molecular weight of 55 kDa, an isoelectric point of 4.3 and contains a pleckstrin homology (PH) domain and a src homology 3 (SH3) domain. In addition to isolated nucleic acids molecules encoding SKAP55 protein, the invention provides antisense nucleic acid molecules, recombinant expression vectors containing a nucleic acid molecule of the invention, host cells into which the expression vectors have been introduced and non-human transgenic animals carrying a SKAP55 transgene. The invention further provides isolated SKAP55 proteins and peptides, SKAP55 fusion proteins and anti-SKAP55 antibodies. Methods of using the SKAP55 compositions of the invention are also disclosed, including methods for detecting SKAP55 protein or mRNA in a biological sample, methods of modulating SKAP55 activity in a cell, and methods for identifying agents that modulate an interaction between SKAP55 and Fyn.

27 Claims, 3 Drawing Sheets

```
  1  TCGCCTTCCAGCCCGTCCGCGCCTCCGACCAGGGCCCCCGTCCCGCCTCTCCCG                                            60

61  CCCAGCCAAATGCAGGCCGCCGCCCTCCCTGAGGAGATCCGTTGGCTCCTGGAAGATGCT                                     120
                M  Q  A  A  A  L  P  E  E  I  R  W  L  L  E  D  A

121  GAAGAGTTTCTGGCAGAAGGTTTGCGGAATGAGAACCTCAGCGCTGTTGCAAGGGATCAC                                     180
      E  E  F  L  A  E  G  L  R  N  E  N  L  S  A  V  A  R  D  H

181  AGAGACCATATTCTACGGGGCTTTCAAATGCCAAATCAAAGCCAGGTACTATTGGGATTTTCAG                                 240
      R  D  H  I  L  R  G  F  Q  Q  I  K  A  R  Y  Y  W  D  F  Q

241  CCCCAAGGGGAGACATTGGACAGGACAGCTCTGATGATAATCACAGCGGGACTCTTGGC                                      300
      P  Q  G  G  D  I  G  Q  D (S) S  D  D  N  H  S  G  T  L  G

301  CTGTCCCTCACAATCCGATGCACCCCTTTTGTCAGATTATCAGGATGAGGGAATGGAAGAC                                    360
      L  S  L  T  S  D  A  P  F  L  S  D  Y  Q  D  E  G  M  E  D

361  ATCGTAAAAGGAGCTCAAGAACTTGATAACGTAATCAAGCAAGGATACTTGGAGAAGAAA                                     420
      I  V  K  G  A  Q  E  L  D | N  V  I  K  Q  G  Y  L  E  K  K |

421  AGCAAAGATCATAGTTTCTTTGGATCGGAGTGGCAGAAGCGATGGTGTGTTGTCAGCAGA                                     480
     | S  K  D  H  S  F  F  G  S  E  W  Q  K  R  W  C  V  V  S  R |
```

*FIG. 1*

481  GGTCTCTTCTACTACTATGCTAATGAGAAGAGCAAGCCCAAAGGACCTTCCTCATT  540
      G  L  F  Y  Y  Y  A  N  E  K  S  K  Q  P  K  G  T  F  L  I

541  AAGGGCTACAGTGTACGGATGGCCCCCCACCTGCGAAGAGATTCCAAGAGAATCCTGC  600
      K  G  Y  S  V  R  M  A  P  H  L  R  R  D  S  K  K  E  C

601  TTTGAACTGACCTCCCAGGATAGGCGCACGTATGAGTTTACAGCTACTAGTCCAGCAGAA  660
      F  E  L  S  Q  D  R  R  T  Y  E  F  T  A  T  S  P  A  E

661  GCCAGAGACTGGGTGGATCAAATAAGTTTCTTGTTAAAGGATCTGAGCTCCTTAACCATT  720
      A  R  D  W  V  D  Q  I  S  F  L  L  K  D  L  S  S  L  T  I

721  CCATATGAAGAGGATGAGGAGGAAGAAGAAGAAGAGACATATGATGATATTGATGGT  780
      P  Y  E  E  D  E  E  E  E  E  K  E  E  Y  D  D  I  D  G

781  TTTGACTCCCCAAGTTGTGGTTCCCAGTGCAGACCCCACTATCTTGCCTGGGAGTGTGGGG  840
      F  D  S  P  S  C  G  S  Q  C  R  P  T  I  L  P  G  S  V  G

841  ATAAAAGAGCCTACAGAGGAGAAAGAAGAAGAAGATATTTATGAAGTCTTGCCAGATGAA  900
      I  K  E  P  T  E  E  K  E  E  D  I  Y  E  V  L  P  D  E

901  GAGCATGATCTAGAAGAGGATGAGAGTGGCACTCGACGAAAAGGAGTAGACTATGCCAGT  960
      E  H  D  L  E  E  D  E  S  G  T  R  R  K  G  V  D  Y  A  S

*FIG. 1*
(CONTINUED)

```
 961  TACTACCAGGGGCCTATGGGATTGCCATGGTGACCAGCCAGATGAACTCTCCTTCCAACGG  1020
       Y  Y  Q  G  L  W  D  C  H  G  D  Q  P  D  E  L  S  F  Q  R

1021  GGTGACCTCATCCGTATTCTGAGCAAGGAGTATAACATGTATGGCTGGTGGGTGGGAGAA  1080
       G  D  L  I  R  I  L  S  K  E  Y  N  M  Y  G  W  W  V  G  E

1081  CTGAACAGCCTCGTTGGGATTGTTCCAAAGGAGTATCTCACCACTGCCTTTGAAGTGGAA  1140
       L  N  S  L  V  G  I  V  P  K  E  Y  L  T  T  A  F  E  V  E

1141  GAAAGATGAAACCCAGGAAATATATTCTTCCCTCTCCTCCTTTATGAGGAAACTGATC  1200
       E  R  *

1201  ATCAAAAGTTCCCACTCCCTACTTCTGCACCCACCAACGCCTGACTCCTCTCTTTGCTGA  1260
1261  AGAGACCCAAGTCTCTTGACACCTCAGAGTGACTGTAAGCTACCAGTAAGACAAGTGGGA  1320
1321  AGAGGCACGTTCATCAAACCTGTTACTAAACCTAGTCATAGCTCATCCCCATGTGT      1380
1381  AAATGTGTCCACACAACCATCTGCCTTTTCCACAAGCTTTTCACAAAGAAGGTGAGAG   1440
1441  AGAAGGAAACCTTGGGAGGAGGACATTACTGGTTGTTCTGGCTGGTTTGAAAAGCACAAA  1500
1501  TAAACTTGGGATGTGTGGTTCCTTG                                     1523
```

FIG. 1 (CONTINUED)

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1523 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 70..1146

(xi) SEQUENCE DESCRIPTION: SEQ ID NO:1:

```
TCGCCTTCCA GCCCGTCCGC CTCCCGACCA GGGCCCGCGC CCCGTCCCGC CTCTCTCCCG      60

CCCAGCCAA ATG CAG GCC GCC GCC CTC CCT GAG GAG ATC CGT TGG CTC         108
          Met Gln Ala Ala Ala Leu Pro Glu Glu Ile Arg Trp Leu
            1               5                  10

CTG GAA GAT GCT GAA GAG TTT CTG GCA GAA GGT TTG CGG AAT GAG AAC       156
Leu Glu Asp Ala Glu Glu Phe Leu Ala Glu Gly Leu Arg Asn Glu Asn
         15                  20                  25

CTC AGC GCT GTT GCA AGG GAT CAC AGA GAC CAT ATT CTA CGG GGC TTT       204
Leu Ser Ala Val Ala Arg Asp His Arg Asp His Ile Leu Arg Gly Phe
 30                  35                  40                  45

CAG CAA ATC AAA GCC AGG TAC TAT TGG GAT TTT CAG CCC CAA GGG GGA       252
Gln Gln Ile Lys Ala Arg Tyr Tyr Trp Asp Phe Gln Pro Gln Gly Gly
                 50                  55                  60

GAC ATT GGA CAG GAC AGC TCT GAT GAT AAT CAC AGC GGG ACT CTT GGC       300
Asp Ile Gly Gln Asp Ser Ser Asp Asp Asn His Ser Gly Thr Leu Gly
             65                  70                  75

CTG TCC CTC ACA TCC GAT GCA CCC TTT TTG TCA GAT TAT CAG GAT GAG       348
Leu Ser Leu Thr Ser Asp Ala Pro Phe Leu Ser Asp Tyr Gln Asp Glu
         80                  85                  90

GGA ATG GAA GAC ATC GTA AAA GGA GCT CAA GAA CTT GAT AAC GTA ATC       396
Gly Met Glu Asp Ile Val Lys Gly Ala Gln Glu Leu Asp Asn Val Ile
 95                 100                 105

AAG CAA GGA TAC TTG GAG AAG AAA AGC AAA GAT CAT AGT TTC TTT GGA       444
Lys Gln Gly Tyr Leu Glu Lys Lys Ser Lys Asp His Ser Phe Phe Gly
110                 115                 120                 125

TCG GAG TGG CAG AAG CGA TGG TGT GTT GTC AGC AGA GGT CTC TTC TAC       492
Ser Glu Trp Gln Lys Arg Trp Cys Val Val Ser Arg Gly Leu Phe Tyr
                130                 135                 140

TAC TAT GCT AAT GAG AAG AGC AAG CAG CCC AAA GGG ACC TTC CTC ATT       540
Tyr Tyr Ala Asn Glu Lys Ser Lys Gln Pro Lys Gly Thr Phe Leu Ile
            145                 150                 155

AAG GGC TAC AGT GTA CGG ATG GCC CCC CAC CTG CGA AGA GAT TCC AAG       588
Lys Gly Tyr Ser Val Arg Met Ala Pro His Leu Arg Arg Asp Ser Lys
        160                 165                 170

AAA GAA TCC TGC TTT GAA CTG ACC TCC CAG GAT AGG CGC ACG TAT GAG       636
Lys Glu Ser Cys Phe Glu Leu Thr Ser Gln Asp Arg Arg Thr Tyr Glu
    175                 180                 185

TTT ACA GCT ACT AGT CCA GCA GAA GCC AGA GAC TGG GTG GAT CAA ATA       684
Phe Thr Ala Thr Ser Pro Ala Glu Ala Arg Asp Trp Val Asp Gln Ile
190                 195                 200                 205

AGT TTC TTG TTA AAG GAT CTG AGC TCC TTA ACC ATT CCA TAT GAA GAG       732
Ser Phe Leu Leu Lys Asp Leu Ser Ser Leu Thr Ile Pro Tyr Glu Glu
```

|     |     |     |     |     |     |     |     |     |     |     |     |     |     |     |     |
|---|---|---|---|---|---|---|---|---|---|---|---|---|---|---|---|
|     |     |     |     | 210 |     |     |     |     | 215 |     |     |     |     | 220 |     |
| GAT | GAG | GAG | GAA | GAA | GAA | AAA | GAA | GAG | ACA | TAT | GAT | GAT | ATT | GAT | GGT | 780 |
| Asp | Glu | Glu | Glu | Glu | Glu | Lys | Glu | Glu | Thr | Tyr | Asp | Asp | Ile | Asp | Gly |
|     |     |     | 225 |     |     |     |     | 230 |     |     |     | 235 |     |     |     |
| TTT | GAC | TCC | CCA | AGT | TGT | GGT | TCC | CAG | TGC | AGA | CCC | ACT | ATC | TTG | CCT | 828 |
| Phe | Asp | Ser | Pro | Ser | Cys | Gly | Ser | Gln | Cys | Arg | Pro | Thr | Ile | Leu | Pro |
|     |     | 240 |     |     |     |     | 245 |     |     |     |     | 250 |     |     |     |
| GGG | AGT | GTG | GGG | ATA | AAA | GAG | CCT | ACA | GAG | GAG | AAA | GAA | GAA | GAA | GAT | 876 |
| Gly | Ser | Val | Gly | Ile | Lys | Glu | Pro | Thr | Glu | Glu | Lys | Glu | Glu | Glu | Asp |
|     | 255 |     |     |     | 260 |     |     |     |     | 265 |     |     |     |     |     |
| ATT | TAT | GAA | GTC | TTG | CCA | GAT | GAA | GAG | CAT | GAT | CTA | GAA | GAG | GAT | GAG | 924 |
| Ile | Tyr | Glu | Val | Leu | Pro | Asp | Glu | Glu | His | Asp | Leu | Glu | Glu | Asp | Glu |
| 270 |     |     |     |     | 275 |     |     |     | 280 |     |     |     |     | 285 |     |
| AGT | GGC | ACT | CGA | CGA | AAA | GGA | GTA | GAC | TAT | GCC | AGT | TAC | TAC | CAG | GGC | 972 |
| Ser | Gly | Thr | Arg | Arg | Lys | Gly | Val | Asp | Tyr | Ala | Ser | Tyr | Tyr | Gln | Gly |
|     |     |     | 290 |     |     |     |     | 295 |     |     |     |     | 300 |     |     |
| CTA | TGG | GAT | TGC | CAT | GGT | GAC | CAG | CCA | GAT | GAA | CTC | TCC | TTC | CAA | CGG | 1020 |
| Leu | Trp | Asp | Cys | His | Gly | Asp | Gln | Pro | Asp | Glu | Leu | Ser | Phe | Gln | Arg |
|     |     |     | 305 |     |     |     |     | 310 |     |     |     |     | 315 |     |     |
| GGT | GAC | CTC | ATC | CGT | ATT | CTG | AGC | AAG | GAG | TAT | AAC | ATG | TAT | GGC | TGG | 1068 |
| Gly | Asp | Leu | Ile | Arg | Ile | Leu | Ser | Lys | Glu | Tyr | Asn | Met | Tyr | Gly | Trp |
|     |     | 320 |     |     |     |     | 325 |     |     |     |     | 330 |     |     |     |
| TGG | GTG | GGA | GAA | CTG | AAC | AGC | CTC | GTT | GGG | ATT | GTT | CCA | AAG | GAG | TAT | 1116 |
| Trp | Val | Gly | Glu | Leu | Asn | Ser | Leu | Val | Gly | Ile | Val | Pro | Lys | Glu | Tyr |
|     | 335 |     |     |     |     | 340 |     |     |     |     | 345 |     |     |     |     |
| CTC | ACC | ACT | GCC | TTT | GAA | GTG | GAA | GAA | AGA | TGAAACCCAG | GAAATATATT |     |     |     |     | 1166 |
| Leu | Thr | Thr | Ala | Phe | Glu | Val | Glu | Glu | Arg |
| 350 |     |     |     |     | 355 |

CTTCCCTCTC TCCTCCTTTA TGAGGAAACT GATCATCAAA AGTTCCCACT CCCTACTTCT  1226

GCACCCACCA ACGCCTGACT CCTCTCTTTG CTGAAGAGAC CCAAGTCTCT TGACACCTCA  1286

GAGTGACTGT AAGCTACCAG TAAGACAAGT GGGAAGAGGC ACGTTCATCA AACCTGTTAC  1346

TAAACCAGCC TAGTCATAGC TCATCCCCAT GTGTAAATGT GTCCACACAA CCACATCTGC  1406

CTTTTCCACA AGCTTTTCAC AAAGAAGGTG AGAGAGAAGG AAACCTTGGG AGGAGGACAT  1466

TACTGGTTGT TCTGGCTGGT TTGAAAAGCA CAAATAAACT TGGGATGTGG TTCCTTG     1523

(2) INFORMATION FOR SEQ ID NO:2:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:2:

| Met | Gln | Ala | Ala | Ala | Leu | Pro | Glu | Glu | Ile | Arg | Trp | Leu | Leu | Glu | Asp |
|---|---|---|---|---|---|---|---|---|---|---|---|---|---|---|---|
| 1 |     |     |     | 5 |     |     |     |     | 10 |     |     |     |     | 15 |     |
| Ala | Glu | Glu | Phe | Leu | Ala | Glu | Gly | Leu | Arg | Asn | Glu | Asn | Leu | Ser | Ala |
|     |     |     | 20 |     |     |     |     | 25 |     |     |     |     | 30 |     |     |
| Val | Ala | Arg | Asp | His | Arg | Asp | His | Ile | Leu | Arg | Gly | Phe | Gln | Gln | Ile |
|     |     | 35 |     |     |     |     | 40 |     |     |     |     | 45 |     |     |     |
| Lys | Ala | Arg | Tyr | Tyr | Trp | Asp | Phe | Gln | Pro | Gln | Gly | Gly | Asp | Ile | Gly |
|     | 50 |     |     |     |     | 55 |     |     |     |     | 60 |     |     |     |     |
| Gln | Asp | Ser | Ser | Asp | Asp | Asn | His | Ser | Gly | Thr | Leu | Gly | Leu | Ser | Leu |
| 65 |     |     |     |     | 70 |     |     |     |     | 75 |     |     |     |     | 80 |
| Thr | Ser | Asp | Ala | Pro | Phe | Leu | Ser | Asp | Tyr | Gln | Asp | Glu | Gly | Met | Glu |
|     |     |     |     | 85 |     |     |     |     | 90 |     |     |     |     | 95 |     |

```
Asp Ile Val Lys Gly Ala Gln Glu Leu Asp Asn Val Ile Lys Gln Gly
            100                 105                 110

Tyr Leu Glu Lys Lys Ser Lys Asp His Ser Phe Phe Gly Ser Glu Trp
            115                 120                 125

Gln Lys Arg Trp Cys Val Val Ser Arg Gly Leu Phe Tyr Tyr Tyr Ala
            130                 135                 140

Asn Glu Lys Ser Lys Gln Pro Lys Gly Thr Phe Leu Ile Lys Gly Tyr
145                 150                 155                 160

Ser Val Arg Met Ala Pro His Leu Arg Arg Asp Ser Lys Lys Glu Ser
                165                 170                 175

Cys Phe Glu Leu Thr Ser Gln Asp Arg Arg Thr Tyr Glu Phe Thr Ala
                180                 185                 190

Thr Ser Pro Ala Glu Ala Arg Asp Trp Val Asp Gln Ile Ser Phe Leu
            195                 200                 205

Leu Lys Asp Leu Ser Ser Leu Thr Ile Pro Tyr Glu Glu Asp Glu Glu
            210                 215                 220

Glu Glu Glu Lys Glu Glu Thr Tyr Asp Asp Ile Asp Gly Phe Asp Ser
225                 230                 235                 240

Pro Ser Cys Gly Ser Gln Cys Arg Pro Thr Ile Leu Pro Gly Ser Val
                245                 250                 255

Gly Ile Lys Glu Pro Thr Glu Glu Lys Glu Glu Glu Asp Ile Tyr Glu
            260                 265                 270

Val Leu Pro Asp Glu Glu His Asp Leu Glu Glu Asp Glu Ser Gly Thr
            275                 280                 285

Arg Arg Lys Gly Val Asp Tyr Ala Ser Tyr Tyr Gln Gly Leu Trp Asp
290                 295                 300

Cys His Gly Asp Gln Pro Asp Glu Leu Ser Phe Gln Arg Gly Asp Leu
305                 310                 315                 320

Ile Arg Ile Leu Ser Lys Glu Tyr Asn Met Tyr Gly Trp Trp Val Gly
                325                 330                 335

Glu Leu Asn Ser Leu Val Gly Ile Val Pro Lys Glu Tyr Leu Thr Thr
            340                 345                 350

Ala Phe Glu Val Glu Glu Arg
            355

(2) INFORMATION FOR SEQ ID NO:3:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

Lys Gly Ala Gln Glu Leu Asp Asn Val Ile
1               5                   10

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal
```

```
      (xi) SEQUENCE DESCRIPTION: SEQ ID NO:4:

Asp His Ser Phe Phe Gly Ser Glu Trp Gln
1               5                   10

(2) INFORMATION FOR SEQ ID NO:5:

(i) SEQUENCE CHARACTERISTICS:
          (A) LENGTH: 98 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:5:

Trp Tyr Phe Gly Lys Leu Gly Arg Lys Asp Ala Glu Arg Gln Leu Leu
1               5                   10                  15

Ser Phe Gly Asn Pro Arg Gly Thr Phe Leu Ile Arg Glu Ser Glu Thr
                20                  25                  30

Thr Lys Gly Ala Tyr Ser Leu Ser Ile Arg Asp Trp Asp Asp Met Lys
            35                  40                  45

Gly Asp His Val Lys His Tyr Lys Ile Arg Lys Leu Asp Asn Gly Gly
        50                  55                  60

Tyr Tyr Ile Thr Thr Arg Ala Gln Phe Glu Thr Leu Gln Gln Leu Val
65                  70                  75                  80

Gln His Tyr Ser Glu Arg Ala Ala Gly Leu Cys Cys Arg Leu Val Val
                85                  90                  95

Pro Cys
```

SKAP55 COMPOSITIONS AND METHODS OF USE THEREFOR

BACKGROUND OF THE INVENTION

Stimulation of T lymphocytes by antigen or anti-T cell receptor (TcR) antibodies causes rapid phosphorylation of several cellular proteins on tyrosine residues. Tyrosine phosphorylation signals are prerequisite for all subsequent events of T cell activation, including mobilization of intracellular calcium and the secretion of lymphokines such as interleukin-2 (IL-2). However, the TcR, the TcR-associated CD3 complex and ζ chain are devoid of intrinsic catalytic properties. This suggests that TcR-induced tyrosine phosphorylation is mediated through recruitment of various cytoplasmic protein tyrosine kinases (PTKs). Indeed, accumulating evidence shows that two members of the src family of protein tyrosine kinases, $p56^{lck}$ and $p59^{fyn}$, as well as the Syk-related kinase ZAP-70, are involved in the initiation of the TcR-induced signaling cascade. For reviews on TcR signal transduction, see Perlmutter, R. M. et al. (1993) *Annu. Rev. Immunol.* 11:451–499 and Chan, A. C. et al. (1994) *Annu. Rev. Immunol.* 12:555–592.

The protein tyrosine kinase $p59^{fyn}$ (also referred to as Fyn) is a 59 kilodalton intracellular protein expressed predominantly in neuronal and hematopoietic cells, including T lymphocytes. A number of experiments suggest a role for Fyn in TcR-mediated T cell responses. Using sensitive in vitro kinase assays and mild detergents for solubilization, an association between Fyn and the TcR complex has been demonstrated (see e.g., Samelson, L. E. et al. (1990) *Proc. Natl. Acad. Sci. USA* 87:4358–4362; Sarosi, G. P. et al. (1992) *Int. Immunol.* 4:1211–1217; Gassman, M. et. al. (1992) *Eur. J Immunol.* 22:283–286). Moreover, ligation of the TcR has been reported to activate the kinase activity of Fyn in various human T cell lines (Tsygankov, A. Y. et al. (1992) *J. Biol. Chem.* 267:18259–18262; da Silva, A. J. et al. (1992) *Mol. Immunol.* 29:1417–1425; Burkhardt, A. L. et al. (1994) *J. Biol. Chem.* 269:23642–23647). Still further, mature T cell lines that underexpress Fyn have been shown to exhibit TcR signaling defects, namely a reduction of the phosphorylation of proteins on tyrosine residues or a lower mobilization of calcium following TcR/CD3 activation, compared to wild-type cells (Lee, S.-K. et al. (1994) *Int. Immunol.* 6:1621–1627; Rigley, K. et al. (1995) *J. Immunol* 154:1136–1145). A role for Fyn in TcR signaling has also been suggested by genetic studies. For example, thymocytes from transgenic mice expressing high levels of Fyn are hyper-responsive to stimulation via the TcR (Cooke, M. P. et al. (1991) *Cell* 65:281–292). Furthermore, disruption of the fyn gene in mice by homologous recombination results in defective signaling in single positive thymocytes (Appleby, M. W. et al. (1992) *Cell* 70:751–763; Stein, P. L. et al. (1992) *Cell* 70:741–750).

Structurally, Fyn is a member of the src family of PTKs, exhibiting a src homology 2 (SH2) domain, responsible for association with phosphotyrosine-containing peptides, and a src homology 3 (SH3) domain, thought to mediate binding to proline-rich peptides. A limited number of proteins have been shown to interact with Fyn through its SH2 and/or SH3 domain upon T cell activation. These proteins include Irs-1 (Sun, X. J. et al. (1996) *J. Biol. Chem.* 271:10583–10587), Sek, an Eph family receptor tyrosine kinase (Ellis, C. et al. (1996) *Oncogene* 12:1727–1736), an embryonal protein Efs (Ishino, M. et al. (1995) *Oncogene* 11:2331–2338), the phosphatidyl inositol-3-kinase (Prasad K. V. et al. (1993) *Proc. Natl. Acad. Sci. USA* 90:7366–7370; Pleiman, C. M. et al. (1994) *Science* 263:1609–1612) and the HS1 protein (Baumann, G., et al. (1994) *Eur. J. Immunol.* 24:1799–1807), as well as polypeptides of 62, 82 and 120/130 kDa of unknown identity (da Silva, A. J. et al. (1993) *J. Exp. Med.* 178:2107–2113). Identification and characterization of proteins capable of interacting with Fyn in T cells is important for understanding the role of Fyn in T cell activation and, accordingly, for designing approaches to modulate this process.

SUMMARY OF THE INVENTION

A 55 kDa protein, termed SKAP55, that interacts with the protein tyrosine kinase Fyn has now been isolated and characterized. The amino acid sequence of SKAP55 protein has been determined (shown in SEQ ID NO: 2) and a cDNA encoding SKAP55 protein has been isolated (the nucleotide sequence of which is shown in SEQ ID NO: 1). SKAP55 was isolated based upon its ability to interact with the src homology 2 (SH2) domain of the protein tyrosine kinase Fyn. The SKAP55 amino acid sequence is characterized by the presence of a pleckstrin homology (PH) domain, a src homology 3 (SH3) domain and several potential phosphorylation sites. This invention pertains to isolated compositions of SKAP55 protein and isolated nucleic acid sequences encoding SKAP55, other compositions related thereto and methods of use thereof.

One aspect of the invention pertains to isolated nucleic acid molecules encoding SKAP55, or fragments thereof. In one embodiment, the invention provides an isolated nucleic acid molecule comprising a nucleotide sequence encoding SKAP55 protein. In other embodiments, the isolated nucleic acid molecules comprise a nucleotide sequence encoding a SKAP55 protein pleckstrin homology domain or a SKAP55 protein src homology 3 (SH3) domain. In yet another embodiment, the invention provides an isolated nucleic acid molecule comprising a nucleotide sequence encoding a protein, wherein the protein comprises an amino acid sequence that is homologous to the amino acid sequence of SEQ ID NO: 2 and interacts with Fyn. In yet another embodiment, the invention provides an isolated nucleic acid molecule which hybridizes under stringent conditions to a nucleic acid molecule comprising the nucleotide sequence of SEQ ID NO: 1. In yet another embodiment, the invention provides an isolated nucleic acid molecule comprising the nucleotide sequence of SEQ ID NO: 1. In other embodiments, the isolated nucleic acid comprises the entire coding region of SEQ ID NO: 1 (nucleotide positions 70 to 1146), the pleckstrin homology domain-encoding region of SEQ ID NO: 1 (nucleotide positions 388 to 684), or the SH3 domain-encoding region of SEQ ID NO: 1 (nucleotide positions 967 to 1137). In still other embodiments, the invention provides an isolated nucleic acid molecule encoding the amino acid sequence of SEQ ID NO: 2 or amino acid positions 107 to 205 of the amino acid sequence of SEQ ID NO: 2 (corresponding to the pleckstrin homology domain) or amino acid positions 300 to 356 of the amino acid sequence of SEQ ID NO: 2 (corresponding to the SH3 domain). Isolated nucleic acid molecules encoding SKAP55 fusion proteins and isolated antisense nucleic acid molecules are also encompassed by the invention.

Another aspect of the invention pertains to vectors, such as recombinant expression vectors, containing an nucleic acid molecule of the invention and host cells into which such vectors have been introduced. In one embodiment, such a host cell is used to produce SKAP55 protein by culturing the host cell in a suitable medium. If desired, SKAP55 protein can be then isolated from the host cell or the medium.

Still another aspect of the invention pertains to isolated SKAP55 proteins, or portions thereof. In one embodiment, the invention provides an isolated SKAP55 protein, or a portion thereof that interacts with Fyn. In other embodiments, the invention provides an isolated SKAP55 protein pleckstrin homology domain or an isolated SKAP55 protein SH3 domain. In yet another embodiment, the invention provides an isolated protein which comprises an amino acid sequence homologous to the amino acid sequence of SEQ ID NO: 2 and that interacts with Fyn. In still other embodiments, the invention provides an isolated protein comprising the amino acid sequence of SEQ ID NO: 2, or a portion thereof, such as amino acid positions 107 to 205 (corresponding to the pleckstrin homology domain) or amino acid positions 300 to 356 (corresponding to the SH3 domain). SKAP55 fusion proteins are also encompassed by the invention.

The SKAP55 proteins of the invention, or fragments thereof, can be used to prepare anti-SKAP55 antibodies. Accordingly, the invention further provides an antibody that specifically binds SKAP55 protein. In one embodiment, the antibody is monoclonal. In another embodiment, the antibody is labeled with a detectable substance.

The SKAP55-encoding nucleic acid molecules of the invention can be used to prepare nonhuman transgenic animals which contain cells carrying a transgene encoding SKAP55 protein or a portion of SKAP55 protein. Accordingly, such transgenic animals are also provided by the invention. In one embodiment, the SKAP55 transgene carried by the transgenic animal alters an endogenous gene encoding endogenous SKAP55 protein (e.g., a homologous recombinant animal).

Another aspect of the invention pertains to methods for detecting the presence of SKAP55 protein or mRNA in a biological sample. To detect SKAP55 protein or mRNA, the biological sample is contacted with an agent capable of detecting SKAP55 protein (such as a labeled anti-SKAP55 antibody) or SKAP55 mRNA (such as a labeled nucleic acid probe capable of hybridizing to SKAP55 mRNA) such that the presence of SKAP55 protein or mRNA is detected in the biological sample.

Still another aspect of the invention pertains to methods for modulating SKAP55 activity in a cell. To modulate SKAP55 activity in a cell, the cell is contacted with an agent that modulates SKAP55 activity such that SKAP55 activity in the cell is modulated. In one embodiment, the agent inhibits SKAP55 activity. In another embodiment, the agent stimulates SKAP55 activity. In one embodiment, the agent modulates the activity of SKAP55 protein (e.g., the agent can be an antibody that specifically binds to SKAP55 protein). In another embodiment, the agent modulates transcription of a SKAP55 gene or translation of a SKAP55 mRNA (e.g., the agent can be a nucleic acid molecule having a nucleotide sequence that is antisense to the coding strand of the SKAP55 mRNA or the SKAP55 gene).

Still another aspect of the invention pertains to methods for identifying agents that modulate an interaction between SKAP55 and Fyn. In these methods, SKAP55 (or a Fyn-interacting portion thereof) is combined with Fyn (or a SKAP55-interacting portion thereof, such as the Fyn SH2 domain) in the presence and absence of a test compound. The degree of interaction between SKAP55 and Fyn is determined in the presence and absence of the test compound. A modulatory agent is identified based upon the ability of the test compound to increase or decrease (e.g., stimulate or inhibit) the degree of interaction between SKAP55 and Fyn (as compared to the degree of interaction in the absence of the test compound).

BRIEF DESCRIPTION OF THE DRAWINGS

FIG. 1 shows the complete cDNA sequence and deduced amino acid sequence of human SKAP55 (SEQ ID NOs: 1 and 2, respectively). The pleckstrin-homology (PH) domain is boxed. The SH3 domain is double underlined. YXXL-like sequences that are potential SH2 domain binding sites are indicated by dashed lines. Putative phosphorylation sites are circled.

DETAILED DESCRIPTION OF THE INVENTION

This invention pertains to a 55 kDa protein, termed SKAP55, that interacts with the protein tyrosine kinase Fyn. Immunoprecipitations using an anti-p59$^{fyn}$ antiserum identified a 55 kDa protein that coimmunoprecipitated with Fyn (see Example 1). A fusion protein containing only the SH2 domain of Fyn (GST-Fyn-SH2) was demonstrated to also precipitate this 55 kDa protein, which enabled large scale purification of the protein (see Example 2). Using partial amino acid sequence information, a cDNA encoding the 55 kDa protein, SKAP55 protein, was isolated and characterized (see Example 3). The SKAP55 protein was found to contain a pleckstrin homology (PH) domain, a src homology 3 (SH3) domain, two putative SH2 domain binding sites and several potential phosphorylation sites. Examination of the tissue expression pattern of SKAP55 mRNA revealed that the SKAP55 transcript is preferentially expressed in lymphatic organs (see Example 4). SKAP55 protein was demonstrated to be constitutively phosphorylated on tyrosine(s) and to preferentially associate with the SH2 domain of Fyn (see Example 5).

So that the invention may be more readily understood, certain terms are first defined.

As used herein, the term "Fyn" (also referred to interchangeably as p59$^{fyn}$) refers to a 59 kDa protooncoprotein that is a member of the src family of protein tyrosine kinases and is intended to include the neuronal (Fyn(B)) and hematopoietic (Fyn(T)) isoforms, which differ as a result of alternative splicing (Kawakami, T. et al. (1986) *Mol. Cell. Biol.* 6:4195; Cooke, M. P. and Perlmutter, R. M. (1989) *New Biologist* 1:66–74).

As used herein the term "pleckstin homology domain" (abbreviated as PH domain) refers to a protein domain, typically about 100 amino acids in length and conserved among a variety of proteins involved in signal transduction, that has been implicated in mediating protein-protein interactions, including binding to G-proteins and inositol-phosphates. For review articles on PH domains, see Ingley, E. and Hemmings, B. A. (1994) *J. Cell. Biochem.* 56:436–443 and Shaw, G. (1996) *Bioessays* 18:35–46.

As used herein, the term "src homology 2 domain" (abbreviated as SH2 domain) refers to a protein domain, typically of about 100 amino acids in length and conserved among a variety of cytoplasmic signaling proteins (including Fyn), that binds phosphotyrosine containing peptides. For a review article on SH2 domains, see Koch, C. A. et al. (1991) *Science* 252:668–674 (which also discloses and compares the amino acid sequences of many different SH2 domains). The amino acid sequence of the Fyn SH2 domain is shown in SEQ ID NO: 5.

As used herein, the term "src homology 3 domain" (abbreviated SH3 domain) refers to a domain, typically about 45 amino acids in length and conserved among a variety of proteins that comprise or associate with the cytoskeleton or membrane, that is thought to mediate binding to proline rich polypeptides. For a review article on SH3 domains, see Koch, C. A. et al. (1991) *Science* 252:668–674. See also Mayer, B. J. et al. (1988) *Nature* 332:272.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA.

As used herein, an "isolated nucleic acid molecule" refers to a nucleic acid molecule that is free of gene sequences which naturally flank the nucleic acid in the genomic DNA of the organism from which the nucleic acid is derived (i.e., gene sequences that are located adjacent to the isolated nucleic molecule in the genomic DNA of the organism from which the nucleic acid is derived). For example, in various embodiments, the isolated SKAP55 nucleic acid molecule may contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, may be free of other cellular material.

As used herein, the term "hybridizes under stringent conditions" is intended to describe conditions for hybridization and washing under which nucleotide sequences at least 60% homologous to each other typically remain hybridized to each other. Preferably, the conditions are such that at least sequences at least 65%, more preferably at least 70%, and even more preferably at least 75% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein, e.g., complementary to the coding strand of a double-stranded CDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of cellular material or culture medium when isolated from cells or produced by recombinant DNA techniques, or chemical precursors or other chemicals when chemically synthesized.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibody" and "monoclonal antibody composition", as used herein, refer to a population of antibody molecules that contain only one species of an antigen binding site capable of immunoreacting with a particular epitope of an antigen. A monoclonal antibody composition thus typically displays a single binding affinity for a particular antigen with which it immunoreacts.

Various aspects of the invention are described in further detail in the following subsections:

I. Isolated Nucleic Acid Molecules

One aspect of the invention pertains to isolated nucleic acid molecules that encode SKAP55, or fragments thereof. Most preferably, an isolated nucleic acid molecule of the invention comprises the nucleotide sequence shown in SEQ ID NO: 1. The sequence of SEQ ID NO: 1 corresponds to the human SKAP55 cDNA. This cDNA comprises sequences encoding the SKAP55 protein (i.e., "the coding region", from nucleotides 70–1146), as well as 5' untranslated sequences (nucleotides 1 to 69) and 3' untranslated sequences (nucleotides 1147 to 1523). Alternatively, the nucleic acid molecule may comprise only the coding region of SEQ ID NO: 1 (i.e., nucleotides 70–1146).

Moreover, the nucleic acid molecule of the invention can comprise only a portion of the coding region of SEQ ID NO: 1, for example a fragment encoding a biologically active portion of SKAP55. The term "biologically active portion of SKAP55" is intended to include portions of SKAP55 that retain the ability to interact with Fyn. The ability of portions of SKAP55 to interact with Fyn can be determined in standard in vitro interaction assays, for example using a Fyn-SH2 domain fusion protein (described further in the Examples). Nucleic acid fragments encoding biologically active portions of SKAP55 can be prepared by isolating a portion of SEQ ID NO: 1, expressing the encoded portion of SKAP55 protein or peptide (e.g., by recombinant expression in a host cell) and assessing the ability of the portion to interact with Fyn, in particular the Fyn SH2 domain, for example using a glutathione-S-transferase (GST)-Fyn-SH2 domain fusion protein. In certain embodiments, an isolated nucleic acid fragment of the invention is at least 300 nucleotides in length. More preferably the fragment is 400, 500, 600, 700, 800, 900 or 1000 nucleotides in length. In other embodiments, a fragment comprises a nucleotide sequence encoding a SKAP55 protein pleckstrin homology domain (e.g., comprising nucleotide positions 388 to 684 of SEQ ID NO: 1) or a nucleotide sequence encoding a SKAP55 protein SH3 domain (e.g., comprising nucleotide positions 967–1137 of SEQ ID NO: 1).

The invention further encompasses nucleic acid molecules that differ from SEQ ID NO: 1 (and fragments thereof) due to degeneracy of the genetic code and thus encode the same SKAP55 protein as that encoded by SEQ ID NO: 1. Accordingly, in another embodiment, an isolated nucleic acid molecule of the invention has a nucleotide sequence encoding a protein having an amino acid sequence shown in SEQ ID NO: 2. Moreover, the invention encompasses nucleic acid molecules that encode portions of SEQ ID NO: 2, such as biologically active portions thereof. In certain embodiments, the isolated nucleic acid comprises a nucleotide sequence encoding a SKAP55 protein pleckstrin homology domain (e.g., encoding amino acid positions 107–205 of SEQ ID NO: 2) or a nucleotide sequence encoding a SKAP55 protein SH3 domain (e.g., encoding amino acid positions 300–356 of SEQ ID NO: 2).

A nucleic acid molecule having the nucleotide sequence of SEQ ID NO: 1, or a portion thereof, can be isolated using standard molecular biology techniques and the sequence information provided herein. For example, a human SKAP55 cDNA can be isolated from a cDNA library (e.g., prepared from human blood cells (commercially available from Stratagene) or from human T lymphocytes or the human T cell line Jurkat) using all or portion of SEQ ID NO: 1 as a hybridization probe and standard hybridization techniques (e.g., as described in Sambrook, J., et al. *Molecular Cloning: A Laboratory Manual. 2nd, ed., Cold Spring Harbor Laboratory*, Cold Spring Harbor, N.Y., 1989).

Moreover, a nucleic acid molecule encompassing all or a portion of SEQ ID NO: 1 can be isolated by the polymerase chain reaction using oligonucleotide primers designed based upon the sequence of SEQ ID NO: 1. For example, mRNA can be isolated from human cells (e.g., by the guanidinium-thiocyanate extraction procedure of Chirgwin et al. (1979) *Biochemistry* 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a SKAP55 nucleotide sequence can be prepared by standard synthetic techniques, e.g., using an automated DNA synthesizer.

In addition to the human SKAP55 nucleotide sequence shown in SEQ ID NO: 1, it will be appreciated by those skilled in the art that DNA sequence polymorphisms that lead to changes in the amino acid sequences of SKAP55 may exist within a population (e.g., the human population). Such genetic polymorphism in the SKAP55 gene may exist among individuals within a population due to natural allelic variation. Such natural allelic variations can typically result in 1–5% variance in the nucleotide sequence of the a gene. Any and all such nucleotide variations and resulting amino acid polymorphisms in SKAP55 that are the result of natural allelic variation and that do not alter the functional activity of SKAP55 are intended to be within the scope of the invention. Moreover, nucleic acid molecules encoding SKAP55 proteins from other species, and thus which have a nucleotide sequence that differs from the human sequence of SEQ ID NO: 1 but that is related to the human sequence, are intended to be within the scope of the invention. Nucleic acid molecules corresponding to natural allelic variants and nonhuman homologues of the human SKAP55 cDNA of the invention can be isolated based on their homology to the human SKAP55 nucleic acid molecule disclosed herein using the human cDNA, or a portion thereof, as a hybridization probe according to standard hybridization techniques under stringent hybridization conditions. Accordingly, in another embodiment, an isolated nucleic acid molecule of the invention hybridizes under stringent conditions to the nucleic acid molecule comprising the nucleotide sequence of SEQ ID NO: 1. In certain embodiment, the nucleic acid is at least 300, 400, 500, 600, 700, 800, 900 or 1000 nucleotides in length. Preferably, an isolated nucleic acid molecule of the invention that hybridizes under stringent conditions to the sequence of SEQ ID NO: 1 corresponds to a naturally-occurring nucleic acid molecule. In one embodiment, the nucleic acid encodes natural human SKAP55 protein. In another embodiment, the nucleic acid molecule encodes a natural murine homologue of human SKAP55 protein, such as mouse SKAP55 protein.

In addition to naturally-occurring allelic variants of the SKAP55 sequence that may exist in the population, the skilled artisan will further appreciate that changes may be introduced by mutation into the nucleotide sequence of SEQ ID NO: 1, thereby leading to changes in the amino acid sequence of the encoded protein, without altering the functional activity of the SKAP55 protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of SKAP55 (e.g., the sequence of SEQ ID NO: 2) without altering the functional activity of SKAP55, such as its ability to interact with Fyn or its ability to participate in signal transduction, whereas an "essential" amino acid residue is required for functional activity. Amino acid residues of SKAP55 that are strongly conserved among signal transduction molecules are predicted to be essential in SKAP55 and thus are not likely to be amenable to alteration. For example, analysis of the predicted amino acid structure of human SKAP55 protein indicates that the protein comprises a pleckstrin homology domain (amino acid positions 107 to 205 of SEQ ID NO: 2) and an SH3 domain (amino acid positions 300 to 356 of SEQ ID NO: 2), two domains that are present in a number of signal transduction molecules. Furthermore, SKAP55 protein comprises several potential phosphorylation sites ($Ser_{67}$, $Ser_{161}$, $Ser_{172}$, $Ser_{176}$, $Thr_{181}$, $Ser_{194}$, $Thr_{231}$, $Tyr_{271}$, $Thr_{288}$, $Tyr_{298}$ and $Thr_{352}$) and two potential SH2 domain binding sites (amino acid positions 219 to 235 of SEQ ID NO: 2 and amino acid positions 271 to 274 of SEQ ID NO: 2). Thus, these highly conserved regions and potential functional regions of SKAP55 are not likely to be amenable to mutation. Other amino acid residues, however, (e.g., those outside the aforementioned regions) may not be essential for SKAP55 activity and thus are likely to be amenable to alteration.

Accordingly, another aspect of the invention pertains to nucleic acid molecules encoding SKAP55 proteins that contain changes in amino acid residues that are not essential for SKAP55 activity, e.g., residues outside of the PH domain, SH3 domain, potential phosphorylation sites or potential SH2 domain binding sites. Such SKAP55 proteins differ in amino acid sequence from SEQ ID NO: 2 yet retain SKAP55 activity. In one embodiment, the isolated nucleic acid molecule comprises a nucleotide sequence encoding a protein, wherein the protein comprises an amino acid sequence at least 60% homologous to the amino acid sequence of SEQ ID NO: 2 and interacts with Fyn. Preferably, the protein encoded by the nucleic acid molecule is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

To determine the percent homology of two amino acid sequences (e.g, SEQ ID NO: 2 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., SEQ ID NO: 2) is occupied by the same amino acid residue as the corresponding position in the other sequence (e.g., a mutant form of SKAP55), then the molecules are homologous at that position (i.e., as used herein amino acid "homology" is equivalent to amino acid "identity"). The percent homology between the two sequences is a function of the number of identical positions shared by the sequences (i.e., % homology=# of identical positions/total # of positions×100).

An isolated nucleic acid molecule encoding a SKAP55 protein homologous to the protein of SEQ ID NO: 2 can be created by introducing one or more nucleotide substitutions, additions or deletions into the nucleotide sequence of SEQ ID NO: 1 such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SKAP55 protein is preferably replaced with another amino acid residue from the same side chain family. Alternatively, in another embodiment, mutations can be introduced randomly along all or part of a SKAP55 coding sequence, such as by saturation mutagenesis, and the resultant mutants can be screened for their ability to interact with Fyn (e.g., using a GST-Fyn-SH2 fusion protein) to identify mutants that retain Fyn-interacting ability. Following mutagenesis of SEQ ID NO: 1, the encoded mutant protein can be expressed recombinantly in a host cell and the ability of the mutant protein to interact with Fyn can be determined using an in vitro interaction assay. For example, a recombinant SKAP55 protein (e.g, a mutated or truncated form of SEQ ID NO: 2) can be radiolabeled and incubated with a GST-Fyn-SH2 fusion protein. Glutathione-sepharose beads are then added to the mixture to precipitate the SKAP55-GST-Fyn-SH2 complex, if such a complex is formed. After washing the beads to remove non-specific binding, the amount of radioactive protein associated with the beads is determined and compared to the amount of radioactive protein remaining in the eluate to thereby determine whether the SKAP55 protein is capable of interacting with the Fyn SH2 domain.

Another aspect of the invention pertains to isolated nucleic acid molecules that are antisense to the coding strand of a SKAP55 mRNA or gene. An antisense nucleic acid of the invention can be complementary to an entire SKAP55 coding strand, or to only a portion thereof. In one embodiment, an antisense nucleic acid molecule is antisense to a coding region of the coding strand of a nucleotide sequence encoding SKAP55 (e.g., the entire coding region of SEQ ID NO: 1 comprises nucleotides 70 to 1146). In another embodiment, the antisense nucleic acid molecule is antisense to a noncoding region of the coding strand of a nucleotide sequence encoding SKAP55. In certain embodiments, an antisense nucleic acid of the invention is at least 300, 400, 500, 600, 700, 800, 900 or 1000 nucleotides in length.

Given the coding strand sequences encoding SKAP55 disclosed herein (e.g., SEQ ID NO: 1), antisense nucleic acids of the invention can be designed according to the rules of Watson and Crick base pairing. The antisense nucleic acid molecule may be complementary to the entire coding region of SKAP55 mRNA, or alternatively can be an oligonucleotide which is antisense to only a portion of the coding or noncoding region of SKAP55 mRNA. For example, the antisense oligonucleotide may be complementary to the region surrounding the translation start site of SKAP55 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a SKAP55-encoding nucleic acid can be designed based upon the nucleotide sequence of a SKAP55 cDNA disclosed herein (i.e., SEQ ID NO: 1). For example, a derivative of a Tetrahymena L-19 IVS RNA can be constructed in which the base sequence of the active site is complementary to the base sequence to be cleaved in a SKAP55-encoding mRNA. See for example Cech et al. U.S. Pat. No. 4,987,071; and Cech et. al. U.S. Pat. No. 5,116,742. Alternatively, SKAP55 mRNA can be used to select a catalytic RNA having a specific ribonuclease activity from a pool of RNA molecules. See for example Bartel, D. and Szostak, J. W. (1993) *Science* 261:1411–1418.

Yet another aspect of the invention pertains to isolated nucleic acid molecules encoding SKAP55 fusion proteins. Such nucleic acid molecules, comprising at least a first nucleotide sequence encoding a SKAP55 protein, polypeptide or peptide operatively linked to a second nucleotide sequence encoding a non-SKAP55 protein, polypeptide or peptide, can be prepared by standard recombinant DNA techniques. SKAP55 fusion proteins are described in further detail below in subsection III.

II. Recombinant Expression Vectors and Host Cells

Another aspect of the invention pertains to vectors, preferably recombinant expression vectors, containing a nucleic acid encoding SKAP55 (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., SKAP55 proteins, mutant forms of SKAP55 proteins, SKAP55 fusion proteins and the like).

The recombinant expression vectors of the invention can be designed for expression of SKAP55 protein in prokaryotic or eukaryotic cells. For example, SKAP55 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al, (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111–2118). Such alteration of nucleic acid sequences of the invention can be carried out by standard DNA synthesis techniques.

In another embodiment, the SKAP55 expression vector is a yeast expression vector. Examples of vectors for expression in yeast *S. cerivisae* include pYepSec1 (Baldari. et al, (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, SKAP55 can be expressed in insect cells using baculovirus expression vectors. Baculovirus vectors available for expression of proteins in cultured insect cells (e.g., Sf 9cells) include the pAc series (Smith et al., (1983) *Mol Cell Biol.* 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), the albumin promoter (liver-specific; Pinkert et al. (1987) *Genes Dev.* 1:268–277), neuron-specific promoters (e.g., the neurofilament promoter; Byrne and Ruddle (1989) *Proc. Natl Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to SKAP55 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews-Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, SKAP55 protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning. A Laboratory Manual,* 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding SKAP55 or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) SKAP55 protein. Accordingly, the invention further provides methods for producing SKAP55 protein using the host cells of the invention. In one embodiment, the method comprises culturing the host cell of invention (into which a recombinant expression vector encoding SKAP55 has been introduced) in a suitable medium until SKAP55 is produced. In another embodiment, the method further comprises isolating SKAP55 from the medium or the host cell. In its native form SKAP55 protein is an intracellular protein and, accordingly, recombinant SKAP55 protein can be expressed intracellularly in a recombinant host cell and then isolated from the host cell, e.g., by lysing the host cell and recovering the recombinant SKAP55 protein from the lysate. Alternatively, recombinant SKAP55 protein can be prepared as a extracellular protein by operatively linking a heterologous signal sequence to the amino-terminus of the protein such that the protein is secreted from the host cells. In this case, recombinant SKAP55 protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which SKAP55-coding sequences have been introduced. Such host cells can then be used to create non-human transgenic animals in which exogenous SKAP55 sequences have been introduced into their genome or homologous recombinant animals in which endogenous SKAP55 sequences have been altered. Such animals are useful for studying the function and/or activity of SKAP55 and for identifying and/or evaluating modulators of SKAP55 activity. Accordingly, another aspect of the invention pertains to nonhuman transgenic animals which contain cells carrying a transgene encoding a SKAP55 protein or a portion of a SKAP55 protein. In a subembodiment, of the transgenic animals of the invention, the transgene alters an endogenous gene encoding an endogenous SKAP55 protein (e.g., homologous recombinant animals in which the endogenous SKAP55 gene has been functionally disrupted or "knocked out", or the nucleotide sequence of the endogenous SKAP55 gene has been mutated or the transcriptional regulatory region of the endogenous SKAP55 gene has been altered).

A transgenic animal of the invention can be created by introducing SKAP55-encoding nucleic acid into the male pronuclei of a fertilized oocyte, e.g., by microinjection, and allowing the oocyte to develop in a pseudopregnant female foster animal. The human SKAP55 cDNA sequence of SEQ ID NO: 1 can be introduced as a transgene into the genome of a non-human animal. Alternatively, a nonhuman homologue of the human SKAP55 gene, such as a mouse SKAP55 gene, can be isolated based on hybridization to the human SKAP55 cDNA and used as a transgene. Intronic sequences and polyadenylation signals can also be included in the transgene to increase the efficiency of expression of the transgene. A tissue-specific regulatory sequence(s) can be operably linked to the SKAP55 transgene to direct expression of SKAP55 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the SKAP55 transgene in its genome and/or expression of SKAP55 mRNA in tissues or cells of the animals. A transgenic founder animal can then be used to breed additional animals carrying the transgene. Moreover, transgenic animals carrying a transgene encoding SKAP55 can further be bred to other transgenic animals carrying other transgenes.

To create a homologous recombinant animal, a vector is prepared which contains at least a portion of a SKAP55 gene into which a deletion, addition or substitution has been introduced to thereby alter, e.g., functionally disrupt, the endogenous SKAP55 gene. The SKAP55 gene may be a human gene (e.g., from a human genomic clone isolated from a human genomic library screened with the cDNA of SEQ ID NO: 1), but more preferably, is a non-human homologue of a human SKAP55 gene. For example, a mouse SKAP55 gene can be isolated from a mouse genomic DNA library using the human SKAP55 cDNA of SEQ ID NO: 1 as a probe. The mouse SKAP55 gene then can be used to construct a homologous recombination vector suitable for altering an endogenous SKAP55 gene in the mouse genome. In a preferred embodiment, the vector is designed such that, upon homologous recombination, the endogenous SKAP55 gene is functionally disrupted (i.e., no longer encodes a functional protein; also referred to as a "knock out" vector). Alternatively, the vector can be designed such that, upon homologous recombination, the endogenous SKAP55 gene is mutated or otherwise altered but still encodes functional protein (e.g., the upstream regulatory region can be altered to thereby alter the expression of the endogenous SKAP55 protein). In the homologous recombination vector, the altered portion of the SKAP55 gene is flanked at its 5' and 3' ends by additional nucleic acid of the SKAP55 gene to allow for homologous recombination to occur between the exogenous SKAP55 gene carried by the vector and an endogenous SKAP55 gene in an embryonic stem cell. The additional flanking SKAP55 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced SKAP55 gene has homologously recombined with the endogenous SKAP55 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

III. Isolated SKAP55 Proteins and Anti-SKAP55 Antibodies

Another aspect of the invention pertains to isolated SKAP55 proteins, and portions thereof, such as biologically active portions, as well as peptide fragments suitable as immunogens to raise anti-SKAP55 antibodies. In one embodiment, the invention provides an isolated preparation of SKAP55 protein. Preferably, the SKAP55 protein has an amino acid sequence shown in SEQ ID NO: 2. In other embodiments, the SKAP55 protein is substantially homologous to SEQ ID NO: 2 and retains the functional activity of the protein of SEQ ID NO: 2 yet differs in amino acid sequence due to natural allelic variation or mutagenesis, as described in detail in subsection I above. Accordingly, in another embodiment, the SKAP55 protein is a protein which comprises an amino acid sequence at least 60% homologous to the amino acid sequence of SEQ ID NO: 2 and that interacts with Fyn. Preferably, the protein is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

In other embodiments, the invention provides an isolated portions of the SKAP55 protein, such as an isolated SKAP55 protein pleckstrin homology domain (e.g., amino acid positions 107 to 205 of SEQ ID NO: 2) and an isolated SKAP55 protein SH3 domain (e.g., amino acid positions 300–356 of SEQ ID NO: 2). The invention further provides a portion of a SKAP55 protein that interacts with Fyn. As demonstrated in the examples, SKAP55 protein preferentially interacts with the SH2 domain of Fyn and, based on analysis of the amino acid sequence of SKAP55, two putative SH2 domain binding sites have been identified within SKAP55. These regions encompass amino acid positions 219 to 235 of SEQ ID NO: 2 and amino acid positions 271 to 274 of SEQ ID NO: 2. Accordingly, peptides encompassing these regions are provided by the invention. An in vitro interaction assay (such as that described above in subsection I utilizing a GST-Fyn-SH2 fusion protein) can be used to determine the ability of such peptides, or peptides encompassing other regions of the SKAP55 protein, to interact with the Fyn SH2 domain.

SKAP55 proteins are preferably produced by recombinant DNA techniques. For example, a nucleic acid molecule encoding the protein is cloned into an expression vector (as described above), the expression vector is introduced into a host cell (as described above) and the SKAP55 protein is expressed in the host cell. The SKAP55 protein can then be isolated from the cells by an appropriate purification scheme using standard protein purification techniques. Alternative to recombinant expression, a SKAP55 polypeptide can be synthesized chemically using standard peptide synthesis techniques. Moreover, native SKAP55 protein can be isolated from cells (e.g., human T cells or the human T cell line Jurkat), for example using a GST-Fyn-SH2 fusion protein to precipitate SKAP55 from cell lysates (as described in Example 2) or by immunoprecipitation using an anti-SKAP55 antibody (discussed further below).

The invention also provides SKAP55 fusion proteins. As used herein, a SKAP55 "fusion protein" comprises a SKAP55 polypeptide operatively linked to a non-SKAP55 polypeptide. A "SKAP55 polypeptide" refers to a polypeptide having an amino acid sequence corresponding to SKAP55 protein, or a peptide fragment thereof (e.g., the SH3 domain thereof or the pleckstrin homology domain thereof), whereas a "non-SKAP55 polypeptide" refers to a polypeptide having an amino acid sequence corresponding to another protein. Within the fusion protein, the term "operatively linked" is intended to indicate that the SKAP55 polypeptide and the non-SKAP55 polypeptide are fused in-frame to each other. The non-SKAP55 polypeptide may be fused to the N-terminus or C-terminus of the SKAP55 polypeptide. For example, in one embodiment the fusion protein is a GST-SKAP55 fusion protein in which the SKAP55 sequences are fused to the C-terminus of the GST sequences. Such fusion proteins can facilitate the purification of recombinant SKAP55. Alternatively, the fusion protein can comprise only a portion of the SKAP55 protein, such as the PH or SH3 domain. For example, a GST-PH fusion protein or a GST-SH3 fusion protein can be prepared by standard recombinant DNA techniques. The GST-PH and GST-SH3 fusion proteins can then be used as "bait" to isolate proteins that interact with the SKAP55 PH and SH3 domains, respectively.

Preferably, a SKAP55 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A SKAP55-encoding nucleic acid can be cloned into such an expression vector such that the fusion moiety is linked in-frame to the SKAP55 protein.

An isolated SKAP55 protein, or fragment thereof, can be used as an immunogen to generate antibodies that bind SKAP55 using standard techniques for polyclonal and monoclonal antibody preparation. The SKAP55 protein can be used to generate antibodies or, alternatively, an antigenic peptide fragment of SKAP55 can be used as the immunogen. An antigenic peptide fragment of SKAP55 typically comprises at least 8 amino acid residues of the amino acid sequence shown in SEQ ID NO: 2 and encompasses an epitope of SKAP55 such that an antibody raised against the peptide forms a specific immune complex with SKAP55. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of SKAP55 that are located on the surface of the protein, e.g., hydrophilic regions. A standard hydrophobicity analysis of the SKAP55 protein sequence shown in SEQ ID NO: 2 can be performed to identify such hydrophilic regions.

A SKAP55 immunogen typically is used to prepare antibodies by immunizing a suitable subject, (e.g., rabbit, goat, mouse or other mammal) with the immunogen. An appropriate immunogenic preparation can contain, for examples, recombinantly expressed SKAP55 protein or a chemically synthesized SKAP55 peptide. The preparation can further include an adjuvant, such as Freund's complete or incomplete adjuvant, or similar immunostimulatory agent. Immunization of a suitable subject with an immunogenic SKAP55 preparation induces a polyclonal anti-SKAP55 antibody response.

Accordingly, another aspect of the invention pertains to anti-SKAP55 antibodies. Polyclonal anti-SKAP55 antibodies can be prepared as described above by immunizing a suitable subject with a SKAP55 immunogen. The anti-SKAP55 antibody titer in the immunized subject can be monitored over time by standard techniques, such as with an enzyme linked immunosorbent assay (ELISA) using immobilized SKAP55. If desired, the antibody molecules directed against SKAP55 can be isolated from the mammal (e.g., from the blood) and further purified by well known techniques, such as protein A chromatography to obtain the IgG fraction. At an appropriate time after immunization, e.g., when the antiSKAP55 antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J. Biol Chem* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983)

*Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a SKAP55 immunogen as described above, and the culture supernatants of the resulting hybridoma cells are screened to identify a hybridoma producing a monoclonal antibody that binds SKAP55.

Any of the many well known protocols used for fusing lymphocytes and immortalized cell lines can be applied for the purpose of generating an anti-SKAP55 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind SKAP55, e.g., using a standard ELISA assay.

Alternative to preparing monoclonal antibody-secreting hybridomas, a monoclonal anti-SKAP55 antibody can be identified and isolated by screening a recombinant combinatorial immunoglobulin library (e.g., an antibody phage display library) with SKAP55 to thereby isolate immunoglobulin library members that bind SKAP55. Kits for generating and screening phage display libraries are commercially available (e.g., the Pharmacia *Recombinant Phage Antibody System*, Catalog No. 27–9400–01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J.* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-SKAP55 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. 5,225,539; Jones et al. (1986) *Nature 321:552–525*; Verhoeyan et al. (1988) *Science* 239:1534; and Beidler et al. (1988) *J. Immunol.* 141:40534060.

An anti-SKAP55 antibody (e.g., monoclonal antibody) can be used to isolate SKAP55 by standard techniques, such as affinity chromatography or immunoprecipitation. An anti-SKAP55 antibody can facilitate the purification of natural SKAP55 from cells and of recombinantly produced SKAP55 expressed in host cells. Moreover, an anti-SKAP55 antibody can be used to detect SKAP55 protein (e.g., in a cellular lysate or cell supernatant). Detection may be facilitated by coupling (i.e., physically linking) the antibody to a detectable substance. Accordingly, in one embodiment, an anti-SKAP55 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

IV. Pharmaceutical Compositions

The SKAP55 proteins and anti-SKAP55 antibodies of the invention can be incorporated into pharmaceutical compositions suitable for administration. Such compositions typically comprise the protein or antibody and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g, a SKAP55 protein or anti-SKAP55 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

V. Methods of the Invention

Another aspect of the invention pertains to a method of using the various SKAP55 compositions of the invention. For example, the invention provides a method for detecting the presence of SKAP55 protein or mRNA in a biological sample. The method involves contacting the biological sample with an agent capable of detecting SKAP55 protein or mRNA such that the presence of SKAP55 protein or mRNA is detected in the biological sample. A preferred agent for detecting SKAP55 mRNA is a labeled nucleic acid probe capable of hybridizing to SKAP55 mRNA. The nucleic acid probe can be, for example, the SKAP55 cDNA of SEQ ID NO: 1, or a portion thereof, such as an oligonucleotide of at least 15, 30, 50, 100, 200, 300, 400, 500, 600, 700, 800, 900 or 1000 nucleotides in length and sufficient to specifically hybridize under stringent conditions to SKAP55 mRNA. A preferred agent for detecting SKAP55 protein is a labeled antibody capable of binding to SKAP55 protein. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of SKAP55 mRNA include Northern hybridizations and in situ hybridizations. Techniques for detection of SKAP55 protein include enzyme linked immunosorbent assays (ELISAs), Western blots, immunoprecipitations and immunofluorescence.

The invention further provides methods for identifying agents that modulate an interaction between SKAP55 and Fyn. In one embodiment, the method comprises:

(a) combining:
  (i) a SKAP55 protein, or Fyn-interacting portion thereof; and
  (ii) Fyn, or a SKAP55-interacting portion thereof; in the presence and absence of a test compound;
(b) determining the degree of interaction between (i) and (ii) in the presence and absence of the test compound; and
(c) identifying an agent that modulates an interaction between SKAP55 and Fyn. Isolated SKAP55 and/or Fyn proteins may be used in the method, or, alternatively, only portions of SKAP55 and/or Fyn may be used. For example, an isolated Fyn SH2 domain (or a larger subregion of Fyn that includes the SH2 domain) can be used as the SKAP55-interacting portion of Fyn. Likewise, an isolated SH2 binding domain of SKAP55 (e.g., encompassing amino acid positions 219 to 235 of SEQ ID NO: 2 or amino acid positions 271 to 274 of SEQ ID NO: 2) can be used as the Fyn-interacting portion of SKAP55. In a preferred embodiment, one or both of (i) and (ii) are fusion proteins, such as GST fusion proteins (e.g., GST-Fyn-SH2 can be used as the SKAP55-interacting portion of Fyn). The degree of interaction between (i) and (ii) can be determined, for example, by labeling one of the proteins with a detectable substance (e.g., a radiolabel), isolating the non-labeled protein and quantitating the amount of detectable substance that has become associated with the non-labeled protein. The assay can be used to identify agents that either stimulate or inhibit the interaction between SKAP55 and Fyn. An agent that stimulates the interaction between SKAP55 and Fyn is identified based upon its ability to increase the degree of interaction between (i) and (ii) as compared to the degree of interaction in the absence of the agent, whereas an agent that inhibits the interaction between SKAP55 and Fyn is identified based upon its ability to decrease the degree of interaction between (i) and (ii) as compared to the degree of interaction in the absence of the agent. Assays systems for identifying agents that modulate SH2 domain-ligand interactions that can be adapted to SKAP55/Fyn in accordance with the present invention are described further in U.S. Pat. No. 5,352,660 by Pawson.

Yet another aspect of the invention pertains to methods of modulating SKAP55 activity in a cell. The modulatory methods of the invention involve contacting the cell with an agent that modulates SKAP55 activity such that SKAP55 activity in the cell is modulated. The agent may act by modulating the activity of SKAP55 protein in the cell or by modulating transcription of the SKAP55 gene or translation of the SKAP55 mRNA. As used herein, the term "modulating" is intended to include inhibiting or decreasing SKAP55 activity and stimulating or increasing SKAP55 activity. Accordingly, in one embodiment, the agent inhibits SKAP55 activity. An inhibitory agent may function, for example, by directly inhibiting SKAP55 activity, by inhibiting an interaction between Fyn and SKAP55, by inhibiting Fyn/SKAP55-mediated signaling, and/or by inhibiting TcR/CD3/Fyn/SKAP55-mediated signaling. In another embodiment, the agent stimulates SKAP55 activity. A stimulatory agent may function, for example, by directly stimulating SKAP55 activity, by promoting an interaction between Fyn and SKAP55, by promoting Fyn/SKAP55-mediated signaling, and/or by promoting TcR/CD3/Fyn/SKAP55-mediated signaling.

A. Inhibitory Agents

According to a modulatory method of the invention, SKAP55 activity is inhibited in a cell by contacting the cell with an inhibitory agent. Inhibitory agents of the invention can be, for example, intracellular binding molecules that act to inhibit the expression or activity of SKAP55. As used herein, the term "intracellular binding molecule" is intended to include molecules that act intracellularly to inhibit the expression or activity of a protein by binding to the protein itself, to a nucleic acid (e.g., an mRNA molecule) that encodes the protein or to a second protein with which the first protein normally interacts (e.g., molecules that bind to Fyn to thereby inhibit the interaction between Fyn and SKAP55). Examples of intracellular binding molecules, described in further detail below, include antisense SKAP55 nucleic acid molecules (e.g., to inhibit translation of SKAP55 mRNA), intracellular anti-SKAP55 antibodies (e.g., to inhibit the activity of SKAP55 protein), molecules that mimic an SH2 binding site of SKAP55 (e.g., to inhibit the interaction of SKAP55 with the SH2 domain of Fyn) and dominant negative mutants of the SKAP55 protein.

In one embodiment, an inhibitory agent of the invention is an antisense nucleic acid molecule that is complementary to a gene encoding SKAP55, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, Reviews-Trends in Genetics, Vol. 1(1) 1986; Askari, F. K. and McDonnell, W. M. (1996) N. Eng. J. Med. 334:316–318; Bennett, M. R. and Schwartz, S. M. (1995) Circulation 92:1981–1993; Mercola, D. and Cohen, J. S. (1995) Cancer Gene Ther. 2:47–59, Rossi, J. J. (1995) Br. Med. Bull. 51:217–225; Wagner, R. W. (1994) Nature 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. An antisense nucleic acid for inhibiting the expression of SKAP55 protein in a cell can be designed based upon the nucleotide sequence encoding the SKAP55 protein (e.g., SEQ ID NO: 1, or a portion thereof), constructed according to the rules of Watson and Crick base pairing.

An antisense nucleic acid can exist in a variety of different forms. For example, the antisense nucleic acid can be an oligonucleotide that is complementary to only a portion of a SKAP55 gene. An antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g phosphorothioate derivatives and acridine substituted nucleotides can be used. To inhibit SKAP55 expression in cells in culture, one or more antisense oligonucleotides can be added to cells in culture media, typically at 200 µg oligonucleotide/ml.

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared as described above for recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is a ribozyme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem.* 118:251–258; Sigurdsson, S. T. and Eckstein, F. (1995) *Trends Biotechnol.* 13:286–289; Rossi, J. J. (1995) *Trends Biotechnol.* 13:301–306; Kiehntopf, M. et al. (1995) *J. Mol. Med.* 73:65–71). A ribozyme having specificity for SKAP55 mRNA can be designed based upon the nucleotide sequence of the SKAP55 cDNA. For example, a derivative of a Tetrahymena L-19 IVS RNA can be constructed in which the base sequence of the active site is complementary to the base sequence to be cleaved in a SKAP55 mRNA. See for example U.S. Pat. Nos. 4,987,071 and 5,116,742, both by Cech et al. Alternatively, SKAP55 mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of SKAP55 in a cell is an intracellular antibody specific for the SKAP55 protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad Sci. USA* 90:7889–7893; Biocca, S. et al. (1994) *Bio/Technology* 12:396–399; Chen, S.-Y. et al. (1994) *Human Gene Therapy* 5:595–601; Duan, L. et al. (1994) *Proc. Natl. Acad. Sci. USA* 91:5075–5079; Chen, S.-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad Sci. USA* 2:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of SKAP55 activity according to the inhibitory methods of the invention, an intracellular antibody that specifically binds the SKAP55 is expressed in the cytoplasm of the cell. To prepare an intracellular antibody expression vector, antibody light and heavy chain cDNAs encoding antibody chains specific for the target protein of interest, e.g., SKAP55, are isolated, typically from a hybridoma that secretes a monoclonal antibody specific for the SKAP55 protein. Hybridomas secreting antiSKAP55 monoclonal antibodies, or recombinant anti-SKAP55 monoclonal antibodies, can be prepared as described above. Once a monoclonal antibody specific for SKAP55 protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or CDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91–3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit SKAP55 activity in a cell, the expression vector encoding the anti-SKAP55 intracellular antibody is introduced into the cell by standard transfection methods, as discussed hereinbefore.

Other inhibitory agents that can be used to inhibit the activity of a SKAP55 protein are chemical compounds that inhibit the interaction between SKAP55 and Fyn. Such compounds can be identified using screening assays that select for such compounds, as described in detail above. Additionally or alternatively, compounds that inhibit the interaction of SKAP55 with the Fyn SH2 domain can be designed using approaches known in the art. SH2 domains are known to interact with phosphotyrosine-containing peptides, with the specificity of a particular SH2 domain for a target binding site being influenced by the amino acid residues surrounding the phosphotyrosine residue (see e.g., Songyang, Z. et al. (1993) *Cell* 72:767–778). Consensus motifs for the binding site of the Fyn SH2 domain have been reported, including Y-$X_1$-$X_2$-(L/I) (wherein $X_1$ and $X_2$ are any amino acids), Y-E-N-(D/E) and Y-E-D-P (Gauen, L. K. et al. (1994) *Mol. Cell. Biol.* 14:3729–41; Chalupny, N. J. et al. (1995) *Eur. J. Immunol.* 25:2978–2984; Ellis, C. et al. (1996) *Oncogene* 12:1727–1736). An optimal binding site motif for the Fyn SH2 domain has been reported to comprise the sequence Y-(E/T)-(E/D/Q)-(I/V/M) (Songyang, Z. et al. (1993) *Cell* 72:767–778). Based on the amino acid sequence of SKAP55, potential SH2 binding sites within SKAP55 are predicted to comprise amino acid positions 219 to 235 of SEQ ID NO: 2 and amino acid positions 271 to 274 of SEQ ID NO: 2.

A competitive inhibitor of SKAP55/Fyn SH2 interactions can be designed based on the amino acid sequence(s) of an SH2 binding site(s) of SKAP55 or the amino acid sequence of a consensus SH2 binding motif for Fyn, such as those described above. In one embodiment, such an inhibitory molecule comprises a nonhydrolyzable phosphonopeptide having an appropriate amino acid sequence for recognition by the Fyn SH2 domain. In this compound, the tyrosine residue within the SH2 binding site is replaced with phosphonomethyl-phenylalanine (Pmp), a nonnatural analogue of phosphotyrosine that is resistant to hydrolysis by phosphatases. Nonhydrolyzable phosphonopeptide inhibitors of SH2 domain interactions can be prepared as described in Domchek, S. M. et al. (1992) *Biochemistry* 31l:9865–9870. Such nonhydrolyzable phosphonopeptides can competitively inhibit the interaction between the Fyn SH2 domain and its target phosphotyrosine-containing binding site within SKAP55 and, moreover, are proteolytically stable (i.e., the phosphonopeptide is resistant to the action of phosphatases). In other embodiments, an inhibitory molecule can comprise a peptidomimetic of the SH2 binding site, such as a benzodiazepine mimetic of a dipeptidyl amide backbone or a boronotyrosine-containing analogue of the phosphotyrosine-containing SH2 binding site (e.g., as described in PCT Publication WO 95/25118 by Bachovchin). These peptidomimetics can competitively inhibit the interaction between the Fyn SH2 domain and its target phosphotyrosine-containing binding site within SKAP55 yet are resistant to degradation.

Yet another form of an inhibitory agent of the invention is an inhibitory form of a SKAP55 protein, also referred to herein as a dominant negative inhibitor. A dominant negative inhibitor can be a form of a SKAP55 protein that retains the ability to interact with the SH2 domain of Fyn but that lacks one or more other functional activities such that the dominant negative form of SKAP55 cannot participate in normal signal transduction. This dominant negative form of a SKAP55 protein may be, for example, a mutated form of SKAP55 in which the SH2 binding site that interacts with the SH2 domain of Fyn is conserved but in which one or more amino acid residues within the PH or SH3 domains are mutated or in which one or more potential phosphorylation sites are mutated. Such dominant negative SKAP55 proteins can be expressed in cells using a recombinant expression vector encoding the mutant SKAP55 protein, which is introduced into the cell by standard transfection methods. In one embodiment, to prepare a dominant negative mutant form of SKAP55, nucleotide sequences encoding amino acid residues 219–235 and/or 271–274 (predicted to be SH2 binding sites) are conserved, whereas at least one amino acid residue within the PH domain (amino acid residues 107–205) and/or the SH3 domain (amino acid residues 300–356) are mutated or deleted. Additionally or alternatively, one or more of the potential phosphorylation sites (e.g., selected from $Ser_{67}$, $Ser_{161}$, $Ser_{172}$, $Ser_{176}$, $Thr_{181}$, $Ser_{194}$, $Thr_{231}$, $Thr_{288}$, $Tyr_{298}$ and $Thr_{352}$) can be mutated or deleted. Mutation or deletion of specific codons within the cDNA can be performed using standard mutagenesis methods. The mutated cDNA is inserted into a recombinant expression vector, which is then introduced into a cell to allow for expression of the mutated SKAP55 protein. The ability of the mutant SKAP55 protein to interact with Fyn can be assessed using standard in vitro interaction assays, such as that using GST-Fyn-SH2 described above. The effect of the mutant SKAP55 protein on normal T cell signal transduction can be assessed, for example, by expressing the mutant SKAP55 protein in T cells in culture (e.g., peripheral blood T cells or Jurkat cells), stimulating the T cells (e.g., using anti-CD3 antibodies) and measuring at least one indicator of T cell activation (e.g., calcium flux, tyrosine phosphorylation, IL-2 production). A mutant form of SKAP55 that retains the ability to interact with Fyn but that interferes with normal T cell signal transduction when expressed in the T cell can be selected as a dominant negative inhibitor of SKAP55 activity.

B. Stimulatory Agents

According to a modulatory method of the invention, SKAP55 activity is stimulated in a cell by contacting the cell with a stimulatory agent. Examples of such stimulatory agents include active SKAP55 protein and nucleic acid molecules encoding SKAP55 that are introduced into the cell to increase SKAP55 activity in the cell. A preferred stimulatory agent is a nucleic acid molecule encoding a SKAP55 protein, wherein the nucleic acid molecule is introduced into the cell in a form suitable for expression of the active SKAP55 protein in the cell. To express a SKAP55 protein in a cell, typically a SKAP55 cDNA is first introduced into a recombinant expression vector using standard molecular biology techniques, as described herein. A SKAP55 cDNA can be obtained, for example, by amplification using the polymerase chain reaction (PCR) or by screening an appropriate cDNA library as described herein. Following isolation or amplification of SKAP55 CDNA, the DNA fragment is introduced into an expression vector and transfected into target cells by standard methods, as described herein.

Other stimulatory agents that can be used to stimulate the activity of a SKAP55 protein are chemical compounds that promote the interaction between SKAP55 and Fyn. Such compounds can be identified using screening assays that select for such compounds, as described in detail above.

In addition to use of an agent that modulates the expression or activity of SKAP55 protein, the modulatory methods of the invention can involve the use of one or more additional agents that modulate T cell activation. For example, the modulatory methods of the invention can involve the use of an agent that modulates SKAP55 activity in combination with an agent that modulates tyrosine phosphorylation in T cells (e.g., an agent that inhibits protein tyrosine kinase activity, such as herbimycin A, or a derivative or analogue thereof), an agent that modulates intracellular calcium levels in T cells (e.g., a calcium ionophore), a phorbol ester (e.g., PMA), a cytokine that modulates T cell activation (e.g., IL-2 and/or IL-4 and the like. Various agents that modulate T cell activation are known in the art.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent of the invention to modulate SKAP55 activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells can be enriched for example, by positive selection using antibodies to T cell surface markers, for example by incubating cells with a specific primary monoclonal antibody (mAb), followed by isolation of cells that bind the mAb using magnetic beads coated with a secondary antibody that binds the primary mAb. Specific cell populations (e.g., T cells) can also be isolated by fluorescence activated cell sorting according to standard methods. Monoclonal antibodies to T cell-specific surface markers known in the art and many are commercially available. If desired, cells treated in vitro with a modulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that SKAP55 activity in cells of the subject is modulated. The term "subject" is intended to include living organisms in which an immune response can be elicited. Preferred subjects are mammals. Examples of subjects include humans, monkeys, dogs, cats, mice, rats, cows, horses, goats and sheep.

For stimulatory or inhibitory agents that comprise nucleic acids (including recombinant expression vectors encoding SKAP55 protein, antisense RNA, intracellular antibodies or dominant negative inhibitors), the agents can be introduced into cells of the subject using methods known in the art for introducing nucleic acid (e.g., DNA) into cells in vivo. Examples of such methods include:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or pretain as much as E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

A modulatory agent, such as a chemical compound that modulates the SKAP55/Fyn interaction, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above in subsection IV.

Considering the role of Fyn in the initial events of T cell activation and the demonstrated interaction between Fyn and SKAP55 in T cells, modulation of SKAP55 activity in T cells may be beneficial in a variety of clinical situations in which is desirable to modulate T cell immune responses, including immunodeficiencies, infectious diseases (e.g., viral infections), cancer, autoimmune diseases, transplantations (e.g., graft rejection or graft-versus-host disease) and allergies, as discussed further below.

Immunodeficiencies: Stimulation of T cell activation through the use of a modulatory agent that modulates SKAP55 activity may be beneficial in a variety of clinical disorders characterized by general or specific immunodeficiency, including human immunodeficiency virus infection and congenital immunodeficiency diseases.

Infectious Diseases: Stimulation of T cell activation through the use of a modulatory agent that modulates SKAP55 activity may be beneficial in a variety of infectious disease, as a means to promote a T cell response against the infectious agent. Such infectious diseases include bacterial, viral, fungal and parasitic infections.

Cancer: Stimulation of T cell activation through the use of a modulatory agent that modulates SKAP55 activity may be beneficial in a variety of malignancies, as a means to promote a T cell response against malignant cells. Alternatively, for T cell leukemias and lymphomas, inhibition of T cell activation through use of a modulatory agent that modulates SKAP55 activity may be beneficial, as a means to inhibit growth or progression of these malignancies.

Autoimmune Diseases: Inhibition of T cell activation through the use of a modulatory agent that modulates SKAP55 activity may be beneficial in a variety of autoimmune disorders, as a means to downregulate T cell response against autoantigens. It is well known in the art that many autoimmune disorders are the result of inappropriate activation of T cells that are reactive against self tissue and that promote the production of cytokines and autoantibodies involved in the pathology of the diseases. Non-limiting examples of autoimmune diseases and disorders having an autoimmune component that may be treated according to the modulatory methods of the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of a modulatory agent in ameliorating autoimmune diseases can be tested in an animal models of human diseases. Such animal models include experimental allergic encephalomyelitis as a model of multiple sclerosis, the NOD mice as a model for diabetes, the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840–856). A modulatory (i.e., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Transplantation: Inhibition of T cell activation through the use of a modulatory agent that modulates SKAP55 activity may be beneficial in transplantation, as a means to downregulate T cell responses against an allograft or to inhibit graft-versus-host disease. Accordingly, the modulatory methods of the invention can be used both in solid organ transplantation and in bone marrow transplantation.

Allergies: Allergies are mediated through IgE antibodies whose production is regulated by the activity of T cells and the cytokines produced thereby. Accordingly, the modulatory methods of the invention can be used to inhibit T cell activation as a means to downregulate allergic responses. A modulatory agent may be directly administered to the subject or T cells may be obtained from the subject, contacted with an modulatory agent ex vivo, and readministered to the subject. Moreover, in certain situations it may be beneficial to coadminister to the subject the allergen together with the modulatory agent or cells treated with the modulatory agent to desensitize the allergen-specific response.

In addition to the foregoing disease situations, the modulatory methods of the invention may be used for other purposes. For example, the modulatory methods that result in increased T cell activation can be used in the production of T cell cytokines in vitro. Furthermore, the modulatory methods of the invention may be applied to vaccinations to promote T cell responses to an antigen of interest in a subject. That is, a modulatory agent of the invention may be used in combination with a vaccine to promote T cell responses against the vaccinating antigen.

This invention is further illustrated by the following examples which should not be construed as limiting. The contents of all references, patents and published patent applications cited throughout this application are hereby incorporated by reference.

EXAMPLE 1

Analysis of the Fyn Molecular Complex in Human Resting T Cells

In this example, proteins interacting with Fyn were identified by performing immunoprecipitations with anti-p59$^{fyn}$. Freshly prepared human resting T lymphocytes were lysed and the resulting lysate was subjected to immunoprecipitation using anti-p59$^{fyn}$ antiserum. The immune complexes were then subjected to an in vitro kinase assay using radiolabeled adenosine triphosphate (ATP). Finally, the phosphorylated proteins were resolved by two dimensional gel analysis and visualized by autoradiography.

For the immunoprecipitation, $10^7$ human resting T cells were washed once in Tris-buffered saline and lysed in 500 μl of 1% NP40 lysis buffer (150 mM NaCl, 20 mM Tris-HCl pH 7.5, 1% NP40, 1 mM sodium vanadate, 10 mM NaF, 1 mM PMSF, 1 mg/ml aprotinin and 1 mg/ml leupeptin) at 4° C. for 1 hour. The lysate was centrifuged at 15,000 rpm for 15 minutes at 4° C. and the resulting post-nuclear lysate was incubated with anti-p59$^{fyn}$ antiserum for 1 hour at 4° C. The immune complexes were then precipitated with protein A sepharose for 1 hour at 4° C., and the beads subsequently washed 3 times in washing buffer (20 mM Tris-HCl pH 7.5, 150 mM NaCl, 10 mM NaF, 1 mM PMSF, 0.1% NP40).

For the in vitro kinase assay, the beads were then resuspended in 40 μL of kinase buffer (20 mM Tris-HCl pH 7.5, 0.1% NP40, 10 mM $MnCl_2$) supplemented with 10 μCi of γ-$^{32}$P-ATP and the kinase reaction carried out for 20 minutes at room temperature. The kinase reaction was stopped by addition of 1 ml of stop buffer (20 mM Tris-HCl pH7.5, 150 mM NaCl, 0.1% NP40, 20 mM EDTA) and the beads washed 6 times in this latter buffer. Finally, the beads were resuspended in 80 μl of 1% Triton X-100 lysis buffer +8M urea and heated for 10 minutes at 37° C. in order to release the immunoprecipitated proteins. The supernatant was then supplemented with 10 μl of 9×O'Farrel buffer (18% NP40, 3.6% ampholines pH 3.5–9.5 (LKB), 0.9% ampholines pH 6–10 (LKB), 0.27M DTT) and subjected to two dimensional gel electrophoresis.

For two dimensional gel analysis, 1 mm tube gel (pH gradient from 3.5 to 9.5) was subjected to a pre-run step (15 min at 200 V, 30 min at 300 V and 30 min at 400 V). The sample was then loaded and overlayed with the upper tank buffer (100 mM NaOH). The buffer for the lower tank was 0.085% $H_3PO_4$ solution. The isoelectric focusing procedure was performed for 1 h at 200 V, 1 h at 300 V, 15.25 h at 400 V and 1.5 h at 800 V. The gel tube was thereafter equilibrated for 20 minutes at room temperature in Lefkowitz buffer (0.12M Tris-HCl, pH 6.8, 2% SDS, 0.05M DTT, 10% glycerol and 0.02% bromophenol blue) and loaded on a SDS-12% polyacrylamide gel in order to separate the proteins on the second dimension according to their molecular weight. Proteins were then detected by autoradiography. In addition to Fyn, six phosphoproteins were detected. The apparent molecular weights of these six proteins were 120, 85, 70, 55, 54 and 45 kDa. The 54 kDa protein has been identified as α-tubulin.

EXAMPLE 2

Precipitation of Proteins Interacting with the Fyn SH2 Domain

In this example, proteins capable of interacting with the SH2 domain of Fyn were identified by performing precipitations on lysates of pervanadate-treated Jurkat T cells using glutathione-sepharose beads coupled to GST-Fyn-SH2 domain fusion protein. Isolated Fyn SH2 domain was expressed as a glutathione-S-transferase (GST) fusion protein in *E. coli* and coupled to glutathione-conjugated sepharose beads following standard procedures (for example, using a pGEX expression vector (Pharmacia Biotech Inc.) to express the GST fusion protein in *E. coli*; see Smith, D. B. and Johnson, K. S. (1988) *Gene* 67:31–40).

For large scale purification of Fyn SH2-interacting proteins, Jurkat cells from a 3 liter culture (approximately $3 \times 10^9$ cells) were treated with 0.1 mM sodium vanadate +1 mM $H_2O_2$ for 2 minutes at room temperature and concentrated by centrifugation. After one wash in cold Tris-buffered saline, cells were lysed at $3 \times 10^7$ cells/ml in 1% NP40 lysis buffer (described in Example 1) at 4° C. for 1 hour. Post-nuclear lysate was subjected to precipitation with 2 ml of packed glutathione-sepharose beads coupled to the GST-Fyn-SH2 fusion protein. Precipitate was washed four times and the proteins were eluted from the packed beads with one volume of release buffer (150 mM NaCl, 10 mM Tris, 50 mM reduced glutathione, 0.1 mM PMSF, 0.5% NP40, pH7.5) for 15 minutes at room temperature. The eluate (2 ml) was then concentrated in a concentrator Amicon tube by centrifugation for 2 hours at 5,000 g and 4° C., leading to a final volume of 300 µl, and adjusted to 8M urea.

One sixth of the sample was separated by two dimensional gel electrophoresis. After Coomassie blue staining, protein spots of interest were cut out, digested and subjected to microsequencing. A 55 kDa protein was isolated and termed SKAP55. To demonstrate that this SKAP55 protein purified by GST-Fyn-SH2 precipitation corresponded to the 55 kDa protein observed by anti-p59$^{fyn}$ immunoprecipitation, resting T cells were subjected to anti-p59$^{fyn}$ immunoprecipitation and the in vitro kinase assay as described in Example 1. The radiolabeled proteins were incorporated into the GST-Fyn-SH2 precipitate for radioactive "spiking". Proteins were then separated by means of two dimensional electrophoresis. The SKAP55 protein purified by GST-Fyn-SH2 comigrated with the radiolabeled 55 kDa protein obtained by anti-p59$^{Fyn}$ immunoprecipitation. The SKAP55 protein has an apparent molecular weight of 55 kDa and an isoelectric point of 4.3.

EXAMPLE 3

Cloning and Characterization of a cDNA Encoding SKAP55 Protein

In this example, a cDNA encoding SKAP55 was isolated using the polymerase chain reaction (PCR) to obtain a cDNA fragment of about 100 base pairs, followed by screening of a cDNA library with the PCR product to isolate a 1.5 kb cDNA molecule. The nucleotide and deduced amino acid sequences of the isolated SKAP55 cDNA clone were then determined.

Peptides from purified SKAP55 (isolated as described in Example 2) were generated by digestion with endoproteinase-Lys-C (Boerhinger Mannheim), separated by reverse-phase high pressure liquid chromatography, and subjected to amino acid microsequencing. Amino acid sequence was determined for two peptides: KGAQELDNVI (peptide 1) (SEQ ID NO: 3) and DHSFFGSEWQ (peptide 2) (SEQ ID NO: 4). Combinations of degenerative oligonucleotides derived from these peptide sequences were used in polymerase chain reactions (PCRs) using cDNA reverse transcribed from Jurkat mRNA. An approximately 100 base pair PCR product was generated using oligonucleotides derived from peptide 1 and peptide 2 as the 5' and 3' primers, respectively. This PCR product was sequenced and used as a probe to screen a cDNA library derived from human blood (Stratagene). Of several positive clones identified, the longest clone was termed 5.2. DNA sequence was determined by standard DNA sequencing for both strands of clone 5.2, which represents a cDNA of 1524 bp. DNA sequencing of the remaining clones indicated that they were likely derived from the same gene as clone 5.2.

The cDNA and deduced amino acid sequences of clone 5.2 are shown in FIG. 1 and SEQ ID NOs: 1 and 2, respectively. An open reading frame is present beginning at nucleotide 70 and terminating at nucleotide 1147. The 3' terminus contains a polyadenylation signal beginning at nucleotide 1498. The open reading frame gives rise to a 358 amino acid polypeptide with a calculated molecular weight of 41.3 kD, suggesting that additional posttranslational events could be responsible for the detection of the protein in SDS-polyacrylamide gels at an apparent molecular weight of 55 kD. Analysis of the deduced amino acid sequence of the SKAP55 protein indicated that SKAP55 contains a pleckstrin-homology (PH) domain (boxed in FIG. 1) and a putative SH3 domain (double underlined in FIG. 1), as well as YXXL-like sequences (dashed lines in FIG. 1) that are potential SH2 domain binding sites, and several putative phosphorylation sites (circled in FIG. 1).

EXAMPLE 4

Expression of SKAP55 mRNA in Human Tissues

In this example, the expression of SKAP55 mRNA in human tissues was examined by standard Northern blot analyses. Nylon membrane hybridization filters were obtained from ClonTech. Each lane was loaded with 2 µg of poly A+RNA isolated from different human tissues and cells. The nylon membranes were prehybridized for 1 hour at 50° C. in ExpressHyb hybridization solution (ClonTech). Hybridization was performed at 50° C. for 1 hour in ExpressHyb hybridization solution using a radiolabeled probe corresponding to nucleotides 298 to 325 of clone 5.2. Blots were washed 3 times for 20 minutes each at room temperature in 2×SSC+0.05% SDS, and then 3 times for 20 minutes each at 50° C. in 0.1×SSC+0.1% SDS. To visualize SKAP55 mRNA, the blots were exposed for autoradiography. SKAP55 transcripts, migrating at approximately 1.5 kb, were strongly detected in spleen, thymus, testis and peripheral blood lymphocyte (PBL) and more weakly in small intestine, indicating a preferential expression of SKAP55 mRNA in lymphatic organs.

EXAMPLE 5

Constitutive Phosphorylation of SKAP55 Protein on Tyrosine

In this example, constitutive phosphorylation of SKAP55 protein on tyrosine was demonstrated by Western blotting with anti-phosphotyrosine antibody. To isolate SKAP55 protein, 50×10$^6$ resting T cells or Jurkat cells were lysed in 1% NP40 lysis buffer and subjected to precipitation using 50 µl of either glutathione-sepharose beads coupled to GSTFyn-SH2 fusion protein or anti-p59$^{fyn}$ antiserum (using methodologies as described in Examples 1 and 2). After washes, proteins were eluted from the beads in 80 µl of 1% TX100 lysis buffer supplemented with 8M urea for 10 minutes at 37° C. Proteins were resolved by two dimensional gel electrophoresis, and electrophoretically transferred onto nitrocellulose membranes. Membranes were then probed with anti-phosphotyrosine antibody (4G10, 1 µg/ml; UBI) and specific protein spots were revealed by enhanced chemiluminescence (ECL) according to the manufacturers recommendations (Amersham). SKAP55 protein was detected as a phosphotyrosine(s)-containing protein in both resting human T lymphocytes and Jurkat cells. In both cell types, a greater amount of SKAP55 protein was precipitated using the GST-Fyn-SH2 fusion protein than using the anti-p59$^{fyn}$ antiserum, indicating that SKAP55 preferentially interacts with the Fyn SH2 domain.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule at least 300 nucleotide in length which hybridizes under stringent conditions to a nucleic acid molecule comprising the nucleotide sequence of SEQ ID NO: 1, and said stringent conditions being hybridization in 6×sodium chloride/sodium citrate (SSC) at 45° C., followed by washing in 0.2×SSC, 0.1% SDS at 50° C.

2. The isolated nucleic acid molecule of claim 1 which comprises a naturally-occurring nucleotide sequence.

3. The isolated nucleic acid molecule of claim 1 which comprises a human nucleotide sequence.

4. The isolated nucleic acid molecule of claim 1 which comprises a mouse nucleotide sequence.

5. An isolated nucleic acid molecule comprising the nucleotide sequence of SEQ ID NO: 1.

6. An isolated nucleic acid molecule which comprises a nucleotide sequence comprising nucleotide positions 70 to 1146 of SEQ ID NO: 1.

7. An isolated nucleic acid molecule which consists of a nucleotide sequence comprising nucleotide positions 388 to 684 of SEQ ID NO: 1.

8. An isolated nucleic acid molecule which consists of a nucleotide sequence comprising nucleotide positions 967 to 1137 of SEQ ID NO: 1, said nucleic acid molecule comprising at least 300 contiguous nucleotides of SEQ ID NO: 1.

9. An isolated nucleic acid molecule encoding the amino acid sequence of SEQ ID NO: 2.

10. An isolated nucleic acid molecule which encodes amino acid positions 107 to 205 of the amino acid sequence of SEQ ID NO: 2.

11. An isolated nucleic acid molecule which encodes amino acid positions 300 to 356 of the amino acid sequence of SEQ ID NO: 2, said nucleic acid molecule comprising at least 300 contiguous nucleotides of SEQ ID NO: 1.

12. An isolated nucleic acid molecule encoding a fusion protein, wherein said fusion protein comprises the amino acid sequence of SEQ ID NO: 2 operatively linked to a second amino acid sequence.

13. An isolated nucleic acid molecule which is antisense to the coding strand of the nucleic acid molecule of claim 5.

14. A vector comprising the nucleic acid molecule of claim 5.

15. The vector of claim 14, which is a recombinant expression vector.

16. A host cell containing the vector of claim 14.

17. A host cell containing the vector of claim 15.

18. A method for producing a protein comprising culturing the host cell of claim 17 in a suitable medium until a protein encoded by the nucleotide sequence of SEQ ID NO: 1 is produced.

19. The method of claim 18, further comprising isolating the protein from the host cell or the medium.

20. A vector comprising the nucleic acid molecule of claim 9.

21. The vector of claim 20, which is a recombinant expression vector.

22. A host cell containing the vector of claim 20.

23. A host cell containing the vector of claim 21.

24. A method for producing a protein comprising culturing the host cell of claim 21 in a suitable medium until a protein comprising the amino acid sequence of SEQ ID NO: 2 is produced.

25. The method of claim 24, further comprising isolating the protein from the host cell or the medium.

26. An isolated nucleic acid sequence encoding a fusion protein comprising the isolated nucleic acid of claim 7, wherein said isolated nucleic acid encodes an amino acid sequence operably linked to a second amino acid sequence.

27. An isolated nucleic acid sequence encoding a fusion protein comprising the isolated nucleic acid of claim 8, wherein said isolated nucleic acid encodes an amino acid sequence operably linked to a second amino acid sequence.

\* \* \* \* \*